US011913907B2

(12) United States Patent
Valster et al.

(10) Patent No.: US 11,913,907 B2
(45) Date of Patent: Feb. 27, 2024

(54) OBTAINING AN INDICATION ABOUT A FAT CONTENT OF MILK

(71) Applicant: KONINKLIJKE PHILIPS N.V., Eindhoven (NL)

(72) Inventors: Susanne Maaike Valster, Valkenswaard (NL); Kiran Hamilton J. Dellimore, Utrecht (NL); Russell Grim, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 458 days.

(21) Appl. No.: 17/285,118

(22) PCT Filed: Aug. 7, 2019

(86) PCT No.: PCT/EP2019/071240
§ 371 (c)(1),
(2) Date: Apr. 14, 2021

(87) PCT Pub. No.: WO2020/098987
PCT Pub. Date: May 22, 2020

(65) Prior Publication Data
US 2021/0247361 A1 Aug. 12, 2021

Related U.S. Application Data

(63) Continuation-in-part of application No. 16/966,036, filed as application No. PCT/EP2019/050477 on Jan. 10, 2019.

(30) Foreign Application Priority Data

Feb. 2, 2018 (EP) ..................................... 18154980
Nov. 16, 2018 (EP) ..................................... 18206806

(51) Int. Cl.
G01N 29/036 (2006.01)
A61M 1/06 (2006.01)
G01N 33/06 (2006.01)

(52) U.S. Cl.
CPC ........... *G01N 29/036* (2013.01); *A61M 1/064* (2014.02); *G01N 33/06* (2013.01); *A61M 2205/3375* (2013.01); *G01N 2291/022* (2013.01)

(58) Field of Classification Search
CPC ................ G01N 29/036; G01N 33/06; G01N 2291/022; G01N 2291/0228;
(Continued)

(56) References Cited

U.S. PATENT DOCUMENTS

| 4,145,450 A | | 3/1979 | Winder | |
|---|---|---|---|---|
| 4,247,773 A | * | 1/1981 | Nexo | ..................... G01N 33/06 250/341.1 |
| 5,623,095 A | * | 4/1997 | Beller | ................... G01N 29/036 73/61.79 |
| 2005/0059928 A1 | | 3/2005 | Larsson | |
| 2011/0004154 A1 | | 1/2011 | Van Schijndel | |
| 2011/0083494 A1 | | 4/2011 | Van Halsema | |

FOREIGN PATENT DOCUMENTS

| WO | 2009060448 | 5/2009 |
|---|---|---|
| WO | 2013/093739 | 6/2013 |
| WO | 2019/149486 | 8/2019 |

OTHER PUBLICATIONS

International Search Report and Written Opinion dated Oct. 1, 2019 for International Application No. PCT/EP2019/071240 Filed Aug. 7, 2019.

(Continued)

*Primary Examiner* — Tarun Sinha

(57) ABSTRACT

A breast pump device (1) is equipped with or used in conjunction with an acoustic milk expression assessment system (6) for the purpose of obtaining an indication about a fat content of expressed milk. The acoustic milk expression assessment system (6) includes an acoustic sensor (61)

(Continued)

and a processor (62) configured to process an acoustic signal received from the acoustic sensor (61) during operation of the breast pump device (1) when a milk receptacle (4) is used with the device (1). By recording sound during a pumping session, it is possible to determine a frequency shift in the sound of droplets falling down in the receptacle (4) and hitting a surface of the milk contained by the receptacle (4) with respect to a reference situation of a liquid having 0% fat content, which can be taken as a factor in estimating a value related to the fat content of the milk.

15 Claims, 4 Drawing Sheets

(58) Field of Classification Search
CPC ......... G01N 29/4436; G01N 2291/014; G01N 29/46; A61M 1/064; A61M 2205/3375; A61M 1/06
See application file for complete search history.

(56) References Cited

OTHER PUBLICATIONS

International Preliminary Report on Patentability dated Jan. 21, 2020 For International Application No. PCT/EP2019/071240 Filed Aug. 7, 2019.
"Foremilk and Hindmilk: In Quest of an Elusive Arbitrary Switch.", May 10, 2011 http://thefunnyshapedwoman.blogspot.com/2011/05/foremilk-and-hindmilk-in-quest-of.html.
Analytical Armadillo, "Foremilk/Hindmilk and a lot of confusion!", 2010 http://www.analyticalarmadillo.co.uk/2010/07/foremilkhindmilk-and-lot-of-confusion.html.
Mizuno, et al: "Mastitis Is Associated with IL-6 Levels and Milk Fat Globule Size in Breast Milk", Journal of Human Lactation, Sep. 6, 2012.

* cited by examiner

OBTAINING AN INDICATION ABOUT A FAT CONTENT OF MILK

CROSS REFERENCE TO RELATED APPLICATIONS

This application is the U.S. National Phase application under 35 U.S.C. § 371 of International Application No. PCT/EP2019/071240 filed Aug. 7, 2019, which claims the benefit of European Patent Application Number 18206806.4 filed Nov. 16, 2018. These applications are hereby incorporated by reference herein.

FIELD OF THE INVENTION

The invention relates to method, computer program, processor and apparatus of obtaining an indication about a fat content of milk, and to a breast pump device comprising such an apparatus.

BACKGROUND OF THE INVENTION

WO 2013/093739 discloses a method of providing an indication as to the amount of milk remaining in a breast during lactation based on a determined fat content of milk that has been expressed from said breast is disclosed. The method of determining said fat content comprises measuring an optical characteristic of milk following expression and by comparing said measured optical characteristic with data representing a corresponding optical characteristic of a sample of milk having a known fat content to determine the fat content of said expressed milk which is indicative of the amount of milk remaining in the breast.

U.S. Pat. No. 4,145,450 discloses method and apparatus for continuously monitoring and controlling the composition of a stream of milk is disclosed. A portion of the continuous stream of milk is heated and coupled to a vacuum degasser where the gas in the milk is removed. A portion of the milk is then heated to 45° C. and conveyed to a sound velocity test cell. A second portion of the milk is heated to 65° C. and conveyed to a second sound velocity test cell. The rate at which a sound pulse traverses the milk in each of the cells is determined by determining the frequency with which the pulses traverse the milk in each of the test cells. The resulting frequency is proportional to the velocity of sound through the milk. The frequency values are coupled to a computer wherein two simultaneous linear equations are solved to arrive at the percent fat and the percent solids-not-fat in the milk. In the preferred embodiment, the butterfat level in the milk is controlled by controlling the quantity of cream added to skim milk in accordance with the output of the computer. The solids-not-fat level in the milk is also controlled by controlling the quantity of skim milk concentrate added to skim milk in accordance with the output of the computer.

WO 2019/149486, from the same applicant Koninklijke Philips N.V. as the applicant of the present application, and which has a priority date before the priority date of the present application but which only been published after the priority and filing dates of the present application, discloses that a processor may be adapted to perform a calculation aimed at providing a user with a real-time indication of the fat content of expressed breast milk during a pumping session. It is a generally known fact that the foremilk is thinner and has a lower fat content than the hindmilk. Based on the insight that the fat content affects the surface tension, and that this may influence the acoustic signal of milk hitting a surface of the receptacle or a surface of a volume of milk as present in the receptacle, the invention provides a way of determining the fat content of the milk during a pumping session. For example, a user may be provided with a real-time indication whether the expressed milk can be qualified as foremilk or hindmilk, an indication of the fat content of the milk, an indication of the total (average) fat content of the milk, and/or a recommendation about how to make sure that a mixture of foremilk and hindmilk as envisaged is collected in a receptacle so as to have an optimal mixture for a feeding session without needing to take further (mixing) actions.

In general, a breast pump device is a well-known tool for extracting milk from a breast of a lactating woman, or from two breasts simultaneously. Breast pump devices may be used in various situations, for example, if a baby or infant is physically not capable of extracting milk from the breast, or if a mother is separated from her baby or infant and the baby or infant is to be fed with breast milk at a later stage, by the mother or another person. Hence, breast pump devices are used by women to express breast milk at a convenient time, to be stored for later consumption by their/a baby or infant. Breast pump devices may also be helpful in a situation in which it is desired to stimulate and increase milk production in women with a low milk supply or to relieve pressure from engorged breasts.

A breast pump device is typically operated with one or two expression kits. Among other things, an expression kit comprises a breast-receiving funnel for receiving a woman's breast, which funnel may be equipped with pads or the like for massaging the breast in a certain way, and is designed for connection to a vacuum unit for realizing a pressure cycle in the expression kit, by means of which milk expression from the breast is enabled. In practical cases, the vacuum unit comprises an electric vacuum pump device, but manually operated breast pump devices are also known and used in practice. The fact is that by generating a pressure cycle, particularly a vacuum cycle, possibly accompanied by a certain way of massaging the breast, a simulation of a feeding action is obtained, which triggers the necessary let-down reflex in the lactating woman using the breast pump device. For the sake of completeness, it is noted that the term "vacuum" as used in this text refers to a relatively low pressure, i.e. a pressure which is significantly lower than ambient pressure.

It is known that at the start of lactation, so-called foremilk is expressed by the breast during a limited time period, followed by so-called hindmilk, an important difference between the two types of breast milk relating to the milk fat concentration, wherein the hindmilk has a considerably higher milk fat content and a considerably lower water content than the foremilk. In order to imitate natural/direct breast feeding as closely as possible in a situation in which extracted breast milk is used, it would therefore be desirable to have two batches of milk, namely a batch being foremilk and another batch being hindmilk. However, the fact is that during a pumping session, it is practically impossible for a user to visually distinguish the hindmilk from the foremilk and to recognize the period during which the composition of the milk changes, so that it is practically impossible for a user to realize collection of milk in the two batches as mentioned.

SUMMARY OF THE INVENTION

In view of the foregoing, it is an object of the invention to provide a breast pump device of a new design, particularly a new design which allows for providing a user with an indication about a fat content of milk, and which preferably allows for warning a user as soon as the type of milk expressed during a pumping session changes from foremilk to hindmilk, so that a user is enabled to collect different types of milk in different receptacles. More in general, it is an object of the invention to provide a method of obtaining an indication about a fat content of milk in a simple yet reliable manner without a need for making a chemical analysis of the milk.

The invention is defined by the independent claims. The dependent claims define advantageous embodiments.

A first embodiment of the invention provides a method of obtaining an indication about a fat content of milk, wherein at least one liquid droplet is made to fall down on a quantity of the milk, wherein the sound of an event of the liquid droplet hitting a surface of the quantity of the milk is detected so as to obtain an acoustic signal of the event, and wherein an analysis of the acoustic signal is performed by executing a routine which is designed to yield an estimation of a value related to the fat content of the milk from the acoustic signal.

The invention relates in particular to the analysis of the acoustic signal, which analysis involves a determination of a frequency spectrum of the acoustic signal.

A second embodiment of the invention provides an apparatus for obtaining an indication about a fat content of milk, for use with a process in which at least one liquid droplet is made to fall down on a quantity of the milk, wherein the sound of an event of the liquid droplet hitting a surface of the quantity of the milk is detected so as to obtain an acoustic signal of the event. The apparatus comprises a processor for performing an analysis of the acoustic signal by executing a routine thereby to yield an estimation of a value related to the fat content of the milk from the acoustic signal.

The apparatus may include an input for receiving the acoustic signal. Thus the acoustic signal may be sensed remotely, and the sensed signal provided to the apparatus. Alternatively, the apparatus may include the acoustic sensor used to obtain the acoustic signal. The apparatus for example includes an output for providing the estimation of a value to a user. In either embodiment, the apparatus may be arranged as an attachment or insert for a milk receptacle, for instance a milk receptacle for use with or in a breast pump. The attachment may be configured as a sleeve or sleeve-like element, for instance to function as a base for the milk receptacle (i.e. the attachment is configured to receive the base of a milk receptacle) or to be put around such a milk receptacle.

The invention involves the insight that the fat content of milk affects the surface tension and the viscosity of a quantity of the milk, and that this may influence the acoustic signal of a liquid droplet hitting a surface of the quantity of the milk. An acoustic signal can be detected and analyzed by using any suitable technique to that end, wherein there is no need for complex measures. The method according to the invention can be carried out in a laboratory, for example. The invention is primarily aimed at providing information about human breast milk, but it is also possible that the invention is applied in the field of analyzing milk obtained from dairy animals such as cows, goats or camels, or other lactating animals. In any case, it is possible to design a breast pump device so as to enable a situation in which the method is performed in the context of the device for obtaining an indication about the fat content of the milk which is expressed during a pumping session. Such a breast pump device may particularly have a function in indicating to a user the time that foremilk changes to hindmilk. The invention is also applicable in milking machines and other equipment for processing animal milk.

As defined in the foregoing, the method according to the invention involves making at least one liquid droplet fall down on a quantity of the milk. On the basis thereof, the method is very well suitable for use in the context of breast pump devices, as normally during operation of such devices, milk is collected in at least one receptacle and milk droplets fall down on a quantity of the milk as present in the at least one receptacle. Thus, for the purpose of using the method according to the invention in the context as mentioned, i.e. the context of breast pump devices, there is no need to make changes in the fundamental design aspects of the devices. Instead, it suffices to add means for detecting sound and means for processing an acoustic signal. In order to obtain a reliable indication about the fat content of milk, it is a practical option to detect the sounds caused by a sequence of liquid droplets hitting the surface of the quantity of the milk, i.e. the sounds caused by a number of liquid droplets hitting the surface of the quantity of the milk one after another with some time in between so that the acoustic signal is a representation of sounds related to the individual liquid droplets, and to perform a step of averaging values in the process of deriving information from the acoustic signal.

In the context of the invention, it is possible that the analysis of the acoustic signal is performed by executing a routine which is designed to yield an estimation of an absolute value related to the fat content of the milk from the acoustic signal. Alternatively, or additionally, it is possible that the analysis of the acoustic signal is performed by executing a routine which is designed to yield an estimation of a relative value related to the fat content of the milk from the acoustic signal. For example, the indication about the fat content of the milk may be provided in the form of a percentage of a predetermined maximum fat content. This may be useful if it is desired to track an actual process of milk expression during a pumping session and make a comparison to one or more previous processes of milk expression. Also, when only a relative value is estimated, it may be so that less computing power is required.

The analysis of the acoustic signal involves a determination of a frequency spectrum of the acoustic signal, i.e. determination of a relation between amplitude and frequency. This may be realized in any suitable manner, such as by performing Fast Fourier Transformation on segments of the acoustic signal. The frequency spectrum can be used for determining a value of the frequency of at least one peak of the frequency spectrum of the acoustic signal and comparing said value to a reference value so as to determine a frequency shift which is taken as a factor in estimating a value related to the fat content of the milk. According to one feasible option, the reference value is established in respect of a liquid having 0% fat content, which does not alter the fact that other options are covered by the invention as well.

Assuming that the volume of the milk is a factor influencing the frequency shift, it is advantageous if a routine which is designed to yield a real-time estimation of a volume of the milk from the acoustic signal is executed first, which routine may involve determination of a value of a time duration between a release moment that the at least one liquid droplet is released to fall down towards the quantity of the milk and a first moment following the release moment that a peak in the acoustic signal appears. Within the framework of the invention, other ways of estimating the volume of the milk are feasible, but it is understood that it is very practical to use the acoustic signal for that purpose as well.

The at least one liquid droplet which is made to fall down on the quantity of the milk to be analyzed may be a droplet of the milk. This is particularly advantageous in the context of breast pump devices, as milk droplets falling down on a quantity of milk are already available. That does not alter the fact that droplets of another type of liquid may be used for the purpose of obtaining an indication about a fat content of the milk in the way of the invention, such as water droplets.

The invention also relates to a breast pump device which uses the apparatus defined above.

An embodiment of the invention provides a breast pump device, comprising:
- an expression kit including a breast-receiving funnel and a milk outlet;
- a pump mechanism;
- an acoustic milk expression assessment system including an acoustic sensor for obtaining the acoustic signal, and the apparatus (for obtaining an indication about a fat content of milk) as defined above; and
- wherein the processor of the apparatus is configured to perform the analysis of the acoustic signal received from the acoustic sensor during operation of the breast pump device.

The analysis involves determination of a frequency spectrum of the acoustic signal. The analysis for example involves determination of a value of the frequency of at least one peak of the frequency spectrum of the acoustic signal and comparison of said value to a reference value so as to determine a frequency shift to be taken as a factor in estimating a value related to the fat content of the milk. The reference value relates to a liquid having 0% fat content.

In more detail, the expression kit may further include an air outlet, the breast pump device may further comprise a vacuum unit configured to realize a pressure cycle in the expression kit, including an air inlet for connection to the air outlet of the expression kit and the pump mechanism for sucking air from the expression kit, through the air outlet of the expression kit and the air inlet of the vacuum unit, and the processor is configured to perform the analysis of the acoustic signal received from the acoustic sensor during operation of the breast pump device when a receptacle is used with the breast pump device for receiving milk from the milk outlet of the expression kit.

The processor is preferably configured to execute a routine which is designed to yield a real-time estimation of a value related to the fat content of the milk from the acoustic signal.

As already explained in the foregoing, the invention relies on applying acoustic techniques for obtaining information which is representative of the fat content of milk. The basis of the invention is found in the insight that the fat content affects the surface tension and the viscosity, and that this may influence the acoustic signal of milk (or another liquid) hitting a surface of a quantity of milk as present in the receptacle. During a pumping session performed by means of the breast pump device, under the influence of the pressure cycle, a repetitive process takes place in which freshly expressed breast milk is allowed to accumulate in the expression kit, at a position upstream of the milk outlet, and is allowed to fall down as milk droplets from that position, through the milk outlet. By detecting the sound of the milk droplets hitting the surface of the quantity of the milk as present in a receptacle which is used for collecting the milk, it is possible to eventually obtain an estimation of a value related to the fat content of the quantity of the milk, without any need to use complex analytical equipment, and without any need to contact the milk to be analyzed.

The processor of the breast pump device may particularly be adapted to perform a calculation aimed at providing a user with a real-time indication of the fat content of expressed breast milk during a pumping session. For example, a user may be provided with a real-time indication whether the expressed milk can be qualified as foremilk or hindmilk, an indication of the fat content of the milk, an indication of the total (average) fat content of the milk, and/or a recommendation about how to make sure that a mixture of foremilk and hindmilk as envisaged is collected in a receptacle so as to have an optimal mixture for a feeding session without needing to take further (mixing) actions.

It is noted that the processor may be of any suitable type, and may be part of a Central Processing Unit (CPU) of the breast pump device which is further configured to control operation of the breast pump device, particularly the pump mechanism.

In order to have optimal ease of use, the invention may involve communication of an automatically determined indication about the fat content to a smartphone or tablet application or computer program, for example, which application or program may further be designed to track other features of a pumping session, such as starting time, duration and expression rate.

Within the framework of the invention, any suitable type of receptacle may be used. As is the case in many conventional situations, the expression kit may be provided with screw thread at a position around the milk outlet, so that it is possible to screw a receptacle to the expression kit at an appropriate position for receiving milk from the expression kit during operation of the breast pump device. Nevertheless, other possibilities of attaching a receptacle to the breast pump device are also covered by the invention.

Various aspects of the method according to the invention are equally applicable to the breast pump device. Two of those aspects are the following: i) it is practical if the routine involves determination of a frequency spectrum of the acoustic signal, wherein optionally Fast Fourier Transformation is applied, and ii) the routine may particularly involve determination of a value of the frequency of at least one peak of the frequency spectrum of the acoustic signal and comparison of said value to a reference value so as to determine a frequency shift to be taken as a factor in estimating a value related to the fat content of the milk, wherein the reference value may relate to a liquid having 0% fat content, or be predetermined in another suitable way.

In the context of the breast pump device, the need of providing a user with an indication that the initially obtained foremilk changes to hindmilk can be fulfilled if the routine involves real-time comparison of an estimated value related to the fat content of the milk to a discrimination value, and of the processor is configured to issue a warning signal the moment that the estimated value related to the fat content of the milk is found to have increased from below to above the discrimination value. Naturally, the discrimination value is chosen such as to be representative of the transition of foremilk to hindmilk. As explained earlier, a user who receives real-time information about the transition of foremilk to hindmilk has the opportunity to change receptacles as used for receiving the milk, so that the foremilk and the hindmilk may actually be separated from each other. This may particularly be useful when it is desired to perform bottle feeding in a more or less natural way, or when it is desired to only use the hindmilk for feeding a baby or infant who is in need of highly nutritious milk.

The invention enables pathology detection, that is to say, detection of conditions which influence the fat content of milk in some way. In view thereof, an embodiment of the breast pump device according to the invention is feasible in which the routine involves comparison of estimated values related to the fat content of the milk in a period of predetermined length from the start of a pumping session to a threshold value, and in which the processor is configured to issue a warning signal when the estimated values related to the fat content of the milk are found to be above the threshold value. Such an embodiment is particularly useful as a tool for mastitis screening, and also as a monitor for treatment efficacy. The fact is that mastitis, i.e. inflammation of the mammary glands in the breast, involves production of abnormally large fat globule sizes in breast milk, and thereby involves an abnormally high fat content of the milk.

It may be advantageous if the processor is further configured to execute a routine which is designed to yield a real-time estimation of a volume of the milk in the receptacle from the acoustic signal. Such a routine may involve determination of a value of a time duration between a release moment and a first moment following the release moment that a peak in the acoustic signal appears, a release moment being a moment at which a release of vacuum takes place during the pressure cycle and at which an associated release of milk from a position in the expression kit and through the milk outlet takes place. A pumping session involves a repetitive process of accumulation of freshly expressed milk in the expression kit and release of the milk through the milk outlet. When vacuum is applied in the pressure cycle, milk is retrieved from a woman's breast. When vacuum is released in the pressure cycle, the milk is allowed to exit the expression kit through the milk outlet, so that it happens at that time that milk falls down, into a receptacle which is used with the breast pump device for receiving milk from the milk outlet, until the milk hits a surface of the receptacle, or, in case that the surface of the receptacle is covered by a quantity of milk, a surface of the milk as present in the receptacle, thereby causing a peak in the acoustic signal. Once the value of the time duration between the release moment and the first moment following the release moment that a peak in the acoustic signal appears is determined, a value is obtained which is directly related to the total milk volume in the receptacle and which is therefore suitable to be used in a process of determining an actual value of the total milk volume in the receptacle.

Preferably, the processor is configured to communicate with an external device or system which is separate from the expression kit and the vacuum unit, and which is configured to provide information to a user. Examples of such an external device or system are a smartphone, a smartwatch, a tablet, a laptop and a computer. The external device or system may be used to run an application/program for providing information about the breast pump device and pumping sessions performed by means of the device to a user. Communication to the external device or system is preferably wireless.

Various positions of the acoustic sensor are feasible within the framework of the invention. A practical and useful position may be a position at the expression kit, downstream of the breast-receiving funnel. In general, a position at which the acoustic signal to be detected is sufficiently strong and free from disturbing influences as much as possible is preferred. The acoustic sensor may comprise a microphone, for example, or a suitable pressure sensor or accelerometer.

The invention also covers an embodiment of the breast pump device in which the acoustic sensor of the acoustic milk expression assessment system is located in an external device or system which is separate from the expression kit and the vacuum unit.

In an example, the breast pump device may further include a holder mechanism for holding the external device or system on the expression kit or a receptacle for use with the breast pump device. In the context of the invention, it has been found that it may be practical not to equip the breast pump device with an acoustic sensor, but to provide an external device or system comprising an acoustic sensor and hold it on the expression kit or the receptacle. For example, use may be made of the microphone which is normally present in a smartphone. By holding the smartphone on the expression kit or the receptacle at an appropriate position, it is possible to detect the acoustic signal which is to be processed for the purpose of obtaining an indication about the fat content of the milk. The holder mechanism may comprise a holder element which is an integral part of an expression kit or the receptacle, but it may even be more practical if a holder element is provided which is connectable to and removable from the expression kit or the receptacle. For example, a sleeve including a microphone may be provided, which sleeve is designed to be wrapped around a receptacle.

In fact, the entire acoustic milk expression assessment system may be incorporated in an external device or system, in which case the external device or system is not only equipped with an acoustic sensor but also with a processor configured to process an acoustic signal received from the acoustic sensor. The various options as described in the foregoing in respect of the configuration of the processor are equally applicable in such a case.

There are Thus Various Possibilities:

The acoustic sensor may be mounted at the expression kit and the processor may be mounted at the pump mechanism.

Alternatively, the expression kit and the pump mechanism may form part of a breast pump and the breast pump device further comprises a user interface device external to the breast pump. In this case, the acoustic sensor may be part of the breast pump and the processor is part of the external user interface device; or both the acoustic sensor and the processor are part of the external user interface device.

The above-described and other aspects of the invention will be apparent from and elucidated with reference to the following detailed description of ways of determining values which are directly related to the fat content of milk and are therefore suitable to be taken as a measure of the fat content of milk. The description is in the context of extracting human breast milk and a breast pump device used in the process, which should not be understood so as to imply that the invention is limited to such context.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
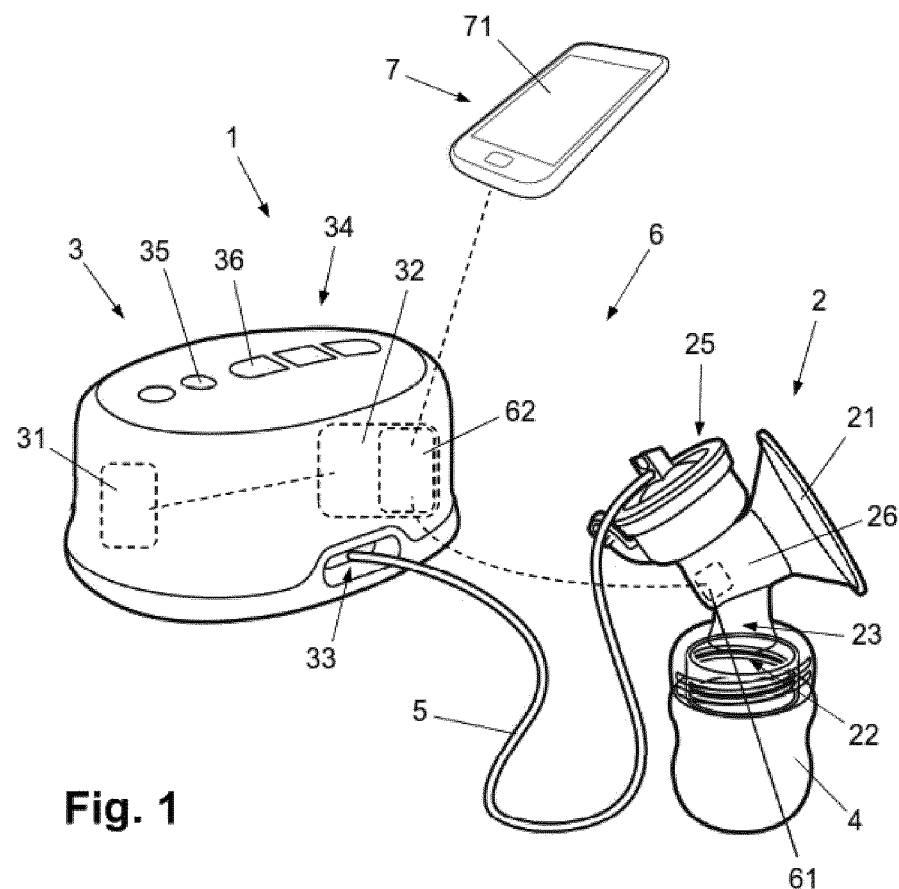
FIG. 1 diagrammatically shows a breast pump device comprising an expression kit, a vacuum unit, and a flexible hose interconnecting the expression kit and the vacuum unit, and also diagrammatically shows a smartphone for receiving information from the breast pump device and displaying information to a user.

The invention is in the field of breast pump devices and is especially applicable to electric breast pump devices. With reference to FIG. 1, a general description of an electric breast pump device will be given first so as to generate a clear picture of contextual aspects of the invention.

The breast pump device 1 comprises an expression kit 2 and a vacuum unit 3 for generating a pressure cycle during which vacuum (low pressure) is alternately generated and released. For the purpose of receiving expressed breast milk during operation of the breast pump device 1, a milk receptacle 4 is used which is connectable to the expression kit 2, e.g. by screwing, thereby closing a lower end of the expression kit 2. The vacuum unit 3 is an electric vacuum unit and comprises an electric pump 31 and an air valve for realizing an alternating vacuum during operation, i.e. during pumping sessions to be performed by means of the breast pump device 1. The pump 31, the air valve and a Central Processing Unit (CPU) 32 for realizing proper operation of the pump 31 and the air valve are designed to function in a manner which is well known in the field of breast pump devices. Therefore, further details of these components will not be explained in the present text, and the same is applicable to other practical aspects of the vacuum unit 3 known per se. The pump 31 is electrically connected to a source of electric power, which may be the mains or a battery, for example. The pump 31 and the CPU 32 are diagrammatically depicted in FIG. 1 as dashed rectangles, whilst the air valve is not shown. A path allowing for exchange of control signals etc. between the pump 31 and the CPU 32 is diagrammatically depicted in FIG. 1 as a dashed line. The path may be realized as any suitable type of communication wire, for example.

The expression kit 2 comprises a breast-receiving funnel 21, an aperture acting as a milk outlet 22, and a milk path 23 from the breast-receiving funnel 21 to the milk outlet 22. The breast-receiving funnel 21 is thus in fluid communication with the milk outlet 22 through the milk path 23. The milk path 23 is closeable by means of a valve assembly 24 (diagrammatically shown in FIG. 2). The breast-receiving funnel 21 can comprise a massage cushion or the like (not shown) for providing a soft and warm feel to the breast and/or imitating a baby's or infant's sucking action.

In FIG. 1, the breast pump device 1 is shown in an assembled condition, in which the vacuum unit 3 is connected to the expression kit 2 through a flexible hose 5, wherein an air inlet 33 of the vacuum unit 3 is connected to an air outlet 25 of the expression kit 2. Such a configuration allows for a remote arrangement of the vacuum unit 3 with respect to the expression kit 2, so that the size of the part of the breast pump device 1 which is to be applied to a woman's breast can be kept within reasonable limits. It is to be noted that the breast pump device 1 can comprise two expression kits 2 for enabling a lactating woman using the breast pump device 1 to extract milk from two breasts at the same time, in which case the expression kits 2 can share a common vacuum unit 3.

Advantageously, as shown, the breast pump device 1 comprises a user interface 34 for allowing a user to control operation of the breast pump device 1. In the shown example, the user interface 34 is arranged on the vacuum unit 3 and enables a user to provide input to the CPU 32. The user interface 34 may be realized in any suitable manner such as through a number of buttons as shown, or through a touch screen, for example. By way of example, it is noted that the user interface 34 may comprise one button 35 for activating a stimulation mode and three buttons 36 for choosing one of three expression settings.

The invention provides a way of estimating the fat content in breast milk by means of the breast pump device 1, i.e. by means of a device which is suitable to be used in a domestic setting as well as in a setting where medical professionals are present, without requiring complex, cumbersome and expensive analytical equipment. To that end, the breast pump device 1 is equipped with an acoustic milk expression assessment system 6 including an acoustic sensor 61 and a processor 62 configured to process an acoustic signal received from the acoustic sensor 61 during operation of the breast pump device 1. In the shown example, the acoustic sensor 61 is a microphone which is integrated in the expression kit 2 at a position along the milk path 23, upstream of the valve assembly 24. That does not alter the fact that another type of acoustic sensor 61 such as a suitable pressure sensor or accelerometer may be used in the breast pump device 1 according to the invention. In the case of the acoustic sensor 61 being a microphone, it is preferred if the microphone is of the unidirectional or cardioid type to minimize external noise and to optimally pick up an acoustic signature of milk droplets falling down in the milk receptacle 4 and hitting a surface of a quantity of milk contained by the receptacle 4. Further, other positions of the acoustic sensor 61 are feasible within the framework of the invention. When it comes to minimizing background noise, adding suitable acoustic shielding is available within the framework of the invention.

Both the acoustic sensor 61 and the processor 62 are diagrammatically depicted in FIG. 1 as dashed rectangles. A path allowing for transmittal of an acoustic signal from the acoustic sensor 61 to the processor 62 is diagrammatically depicted in FIG. 1 as a dashed line. The path is preferably realized in a wireless manner, which should not be understood such as to imply that a wired path is not covered by the invention as well.

The processor 62 may be part of the CPU 32, as indicated in FIG. 1. Besides the breast pump device 1, FIG. 1 shows a smartphone 7 which is used for providing information generated by the processor 62 during operation of the breast pump device 1 to a user. The processor 62 is configured for communicating with the smartphone 7, wherein the smartphone 7 may be used to run an application designed to display relevant information about the breast pump device 1 and pumping sessions performed by means of the breast pump device 1 on the screen 71 of the smartphone 7, and possibly also to receive relevant input from a user, in which case the smartphone 7 serves as a user interface. A path allowing for exchange of information between the processor 62 and the smartphone 7 is diagrammatically depicted in FIG. 1 as a dashed line. The path is preferably realized in a wireless manner, which should not be understood such as to imply that a wired path is not covered by the invention as well.

When it comes to holding a smartphone 7 or other external device or system to a milk receptacle 4, any suitable holder mechanism can be designed and applied. In general, such a suitable holder mechanism may comprise a holder which is designed to wrap around the receptacle 4 securely and which is also capable of securely holding the smartphone 7, wherein it is preferred if the holder can be adapted to use with receptacles 4 of various diameters, for example on the basis of flexible properties.

Additionally, any holder accessory could be devised for the support and positioning of any wireless earbuds/earphones near the desired sound detecting location on a breast pump device 1. The microphone of the earbuds/earphones could be used to collect information suitable for the purpose of estimating a value related to the fat content of the milk instead of the smartphone 7.

A process of detecting an acoustic signal for the purpose of obtaining an indication about the fat content of the milk can be very well performed in a context of a double electric breast pump device, i.e. a breast pump device which is designed to retrieve milk from two breasts simultaneously, and which comprises two expression kits 2. According to a first option, an acoustic sensor 61 could be integrated on each of the two expression kits 2, and the two acoustic signals obtained in that way could be analyzed for finding the information as required. According to a second option, it is possible to use only acoustic sensor 61 on only one of the two expression kits 2, provided that the acoustic sensor 61 is arranged at a position where it is possible to detect the sound of milk droplets falling in each of the receptacles 4 connected to the respective expression kits 2. The milk droplets falling in the one receptacle 4 can be distinguished from the milk droplets falling in the other receptacle 4 on the basis of the amplitude (or another suitable feature) of the detected peaks in the acoustic signal. The fact is that milk droplets falling in the receptacle 4 which is closest to the acoustic sensor 61 can be expected to generate sound at a larger amplitude than milk droplets falling in the receptacle 4 which is at a larger distance. In the context of a double electric breast pump device, it may be advantageous to use a bidirectional or an omnidirectional microphone as the acoustic sensor 61 rather than an unidirectional microphone.

In the following, the way in which the acoustic milk expression assessment system 6 works will be explained, wherein also details of a theoretical background of the functioning principle of the acoustic milk expression assessment system 6 will be given.

Figure 2:
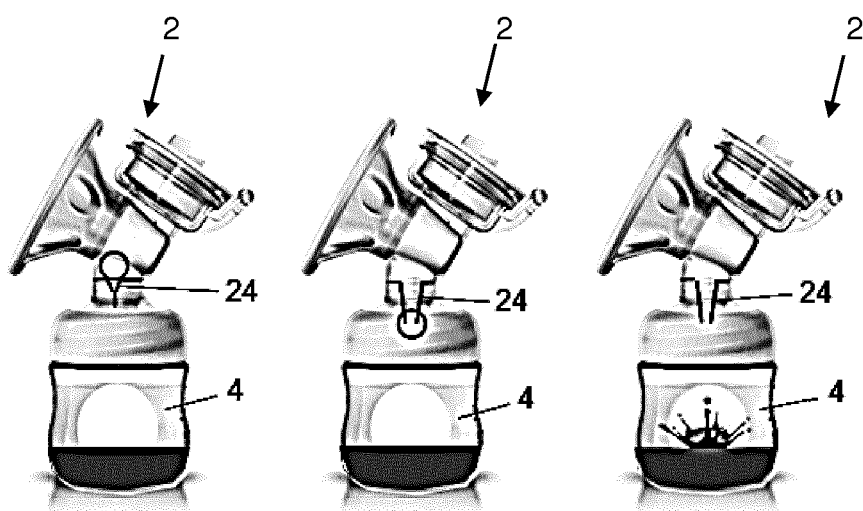
FIG. 2 illustrates various stages of expressed milk being collected in the expression kit, the milk being released towards a receptacle attached to the expression kit, and the milk hitting a surface of a quantity of milk in a receptacle which is partially filled, respectively.

In general, the breast pump device 1 is used to realize milk expression from a woman's breast. To that end, an alternating vacuum (pressure cycle) is applied to the breast. During periods of low pressure, or vacuum, the actual process in which milk is expressed from the breast takes place. Every time that the vacuum is released, freshly expressed milk drops in the receptacle 4. The quantity of milk which falls down from the expression kit 2 is small and may be expected to appear from the expression kit 2 as a droplet. In FIG. 2, the first (most left) representation of an expression kit 2 and a receptacle 4 attached thereto serves to illustrate the fact that during a vacuum period, the valve assembly 24 is closed so that milk is collected above the valve assembly 24. Milk (to be) released from the expression kit 2 is diagrammatically depicted in FIG. 2 as a circle, and the valve assembly 24 is also diagrammatically depicted, by means of a number of lines. In the second representation of an expression kit 2 and a receptacle 4 attached thereto, it is illustrated that when the pressure is released, the milk falls down in the receptacle 4, towards a quantity of milk which is already present in the receptacle 4. The third representation of an expression kit 2 and a receptacle 4 attached thereto serves to illustrate a situation in which the milk which is released from the expression kit 2 ends up on a surface of the quantity of milk contained by the receptacle 4.

It is generally known that the fat content of expressed milk changes during a pumping session. In a first instance, so-called foremilk is expressed, whereas in a later instance, so-called hindmilk is expressed, wherein it is to be noted that the foremilk is thinner and has a lower fat content than the hindmilk, and also that there is no sharp distinction between the foremilk and the hindmilk, as the composition of the milk will change gradually. The foremilk mainly has a function in quenching a baby's or infant's thirst, while the hindmilk mainly has a function in providing a satisfied feeling and stopping hunger. In order to achieve a natural feeding scheme with expressed milk, it is desired to first give foremilk to a baby or infant and then provide the baby or infant with the hindmilk. To that end, the milk should be stored in at least two different receptacles during expression. The receptacle should be switched when the fat content of the milk increases above a certain threshold, indicating the transition from foremilk to hindmilk.

The breast pump device 1 is adapted to automatically estimate in real-time the fat content of human breast milk during expression with the acoustic milk expression assessment system 6, by analyzing the frequency spectrum of the splashes produced by the milk droplets as they fall down in the receptacle 4. An acoustic signal acquired by the acoustic sensor 61 is processed by the processor 62 in order to compute the frequency spectrum. A practical way of doing so involves isolating consecutive milk droplet splash events and performing a Fast Fourier Transformation on droplet signal segments. For example, five to ten events collected with a time frame of about 10 to 20 seconds may be isolated. The spectra for each droplet may be averaged, so that effects of noise and outliers may be reduced. As a result, a mean milk droplet frequency spectrum is obtained.

Preferably, the acoustic signal is used first for the purpose of determining the volume of the milk in the receptacle 4. This can be done by collecting information about the time it takes for milk droplets to fall down from the valve assembly 24 to the surface of the milk as present in the receptacle 4. The acoustic milk expression assessment system 6 may be configured to perform a process of estimating a value related to the fat content of the milk once a certain volume has been reached.

Figure 3:
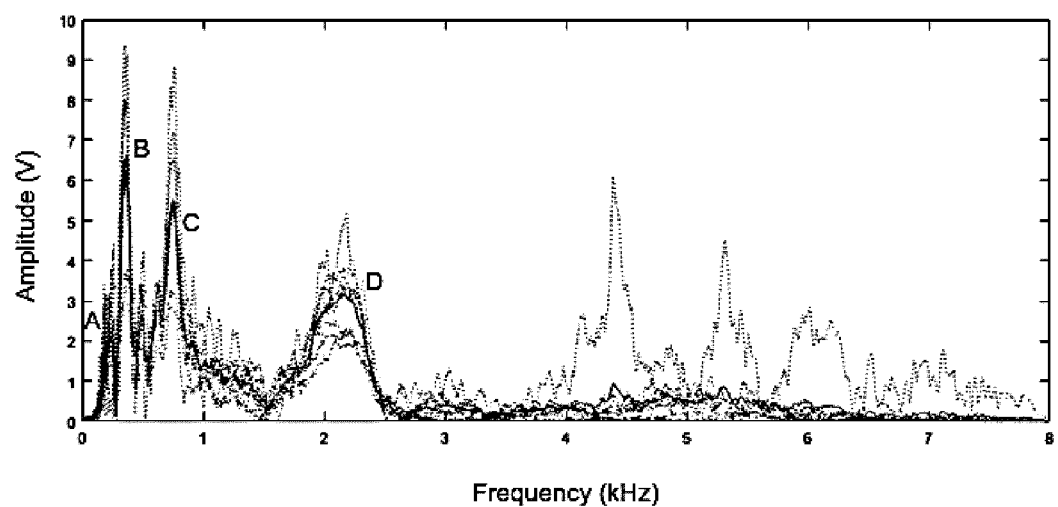
FIG. 3 shows a frequency spectrum as obtained from an experiment in which milk droplets were made to fall down to a quantity of milk and in which sound was detected.

FIG. 3 shows an averaged frequency spectrum experimentally obtained for milk droplets at a volume of milk in the receptacle 4 of 60 ml. In the shown example, to make the milk fat content analysis easier, only the part of the averaged frequency spectrum between 0 and 4 kHz is used. A peak detector is used to isolate the frequency of the main peaks in the averaged milk droplet frequency spectrum. In the frequency spectrum shown in FIG. 3, four main peaks A, B, C and D can be distinguished for the frequency range of 0 to 4 kHz.

A practical way of analyzing the frequency spectrum and the routine (algorithm) followed in the process are explained in the following. It is to be noted that this is one out of a larger number of ways existing within the framework of the invention, particularly one which is aimed at determining the moment in a pumping session that a transition from foremilk to hindmilk takes place.

The routine uses a first order parametric transfer function, according to which two variables, namely volume of milk in the receptacle 4 (V, ml) and measured frequency of the fourth peak D from the milk splash ($f_m$, Hz), are taken in and used to estimate the fat content (F, %), on the basis of the following empirically determined basic formula, wherein $K_1$, $K_2$ and c represent empirically derived constants:

$$F=K_2(fm-(K_1V+c))$$

This transfer function consists of two sub transfer functions, which describe the behavior of the fourth peak D as it reacts to i) volume at 0% fat content (i.e. water) and ii) changes in fat content, wherein $f_w$ represents the expected peak location for 0% fat content (Hz) and $\Delta f$ represents the change in frequency (Hz):

$$fw==K_1V+c$$

$$F=K_2\Delta f$$

In experiments performed in the context of the invention, $K_1$ and c were found by collecting the location of the fourth peak D for eleven different volumes ranging from 50 ml to 150 ml. $K_2$ was found by varying the fat content and observing the location of the same fourth peak D. In this way, in respect of $K_1$ and c, a nonlinear model was found, which is represented by the following equations:

$$f_w=-11.2\ V+2,966$$

for volumes below 80 ml, and $$f_w=-6.2\ V+2,306$$

for volumes above 80 ml. Thus, it appeared that for volumes below 80 ml, $K_1=-11.2$ Hz ml$^{-1}$ and c=2,966 Hz, and that for volumes above 80 ml, $K_1=-6.2$ Hz ml$^{-1}$ and c=2,306 Hz. Further, irrespective of the volume, a suitable value of $K_2$ was found to be 0.075% Hz$^{-1}$.

When the values of $K_1$, $K_2$ and c are used in the basic formula provided earlier, the following model is obtained:

$$V<80\ ml\ F=0.075(f_m+11.2V-2,966)$$

$$V>80\ ml\ F=0.075(f_m+6.2V-2,306)$$

First order models were used in this analysis to approximate the system's behavior. Higher order models, or even alternative nonlinear models such as look-up tables could be used to improve accuracy.

The use of the model is illustrated by means of an example in which the volume is 150 ml and the fourth peak D is found to be at 1,400 Hz when the frequency spectrum from the splash is analyzed. In the example, the estimated absolute value of the fat content turns out to be $$F=0.075(1,400+6.2150-2,306)=1.8\%$$

It is to be noted that other features could be considered, such as ratios of two or more peaks A, B, C, D in the frequency domain and damping coefficients of the envelops of the time domain signals. It may further be possible to establish a "fingerprint" for a given milk formation using a combination of such features.

Figure 4:
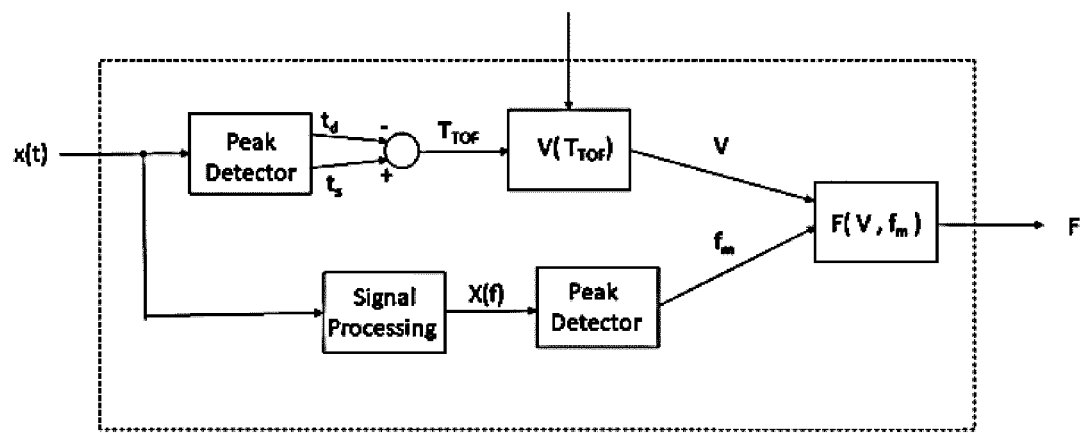
FIG. 4 gives a schematic overview of a system for milk fat content estimation and milk volume estimation.

A schematic overview of a system as described in the foregoing, for milk fat content estimation and also for milk volume estimation by acoustic detection of two droplets released during expression with a double electric breast pump is given in FIG. 4. In FIG. 4, x(t)=splash audio signal, $t_d$=time of opening of the valve assembly 24 (s), $t_s$=time of splash (s), i.e. the time at which a droplet hits the surface of the milk, $T_{TOF}$=time of flight (s), i.e. the time it takes for a droplet to fall down in the receptacle 4 before hitting the surface of the milk, V=volume of the milk in the receptacle 4 (ml), X(f)=frequency spectrum of the splash audio signal, $f_m$=peak location of the milk (Hz), and F=fat content of the milk (%). Further, $V(T_{TOF})$ represents the function which calculates volume from the time of flight, and $F(V,f_m)$ represents the function which calculates fat content from volume and peak location of the milk. Further input to the function which calculates volume from the time of flight is user input about aspects such as the type of receptacle 4, so that geometrical and dimensional factors of the receptacle 4 may be taken into account when the function is performed.

A summary of the basic theory underpinning the invention is now provided to enhance understanding.

The observed peak frequency shift in the averaged droplet frequency spectrum is assumed to occur due to two coupled factors: i) changes in volume as the receptacle 4 is filled with milk, and ii) changes in surface tension/viscosity linked directly to the fact content of the milk. Changes in surface tension arising due to other factors such as mineral content, impurities or temperature are assumed to be negligible and therefore ignored. Temperature can greatly influence surface tension and viscosity, however, it is assumed here that the expressed milk will not undergo a large change in temperature during expression and thus will not vary greatly from about 37° C., i.e. the approximate temperature at which milk is expressed from the human body.

It is further assumed that the volume and fat content factors are additive and can be completely decoupled by separately considering the effect of volume and fat content. Since the volume change effect is two orders of magnitude larger than the fat content change effect, over the functional range of the breast pump device 1, first the magnitude of the volume effect is isolated by comparison with water at the same volume. Water is a useful comparison medium as water contains no fat. This implicitly assumes that if the milk at a given volume is compared with water at the same volume, the frequency of the fourth peak D would be identical if the milk had no fat content. Thus, any difference in the frequency of the fourth peak D for milk and the corresponding peak for water is assumed to only arise from the changes in surface tension/viscosity linked directly to the fat content of the milk. This assumption implies further that the effect of fat content on the surface tension and the viscosity is the same at all milk volumes, i.e. that the fat content will change the frequency spectrum in an identical magnitude and direction at all milk volumes.

In order to confirm the above approach, further details are given of the setting in which the experiments were performed. In the experiments, a pipette, a container, milk, a ml measuring cylinder, a microphone, a clamp stand, and a personal computer with Matlab and Audacity installed were used. The pipette was held 300 mm from the rim of the container by the clamp stand at a slight angle. The pipette was used instead of a pump to allow for better control of droplet formation. The microphone was taped to the bottom of the container. The milk was diluted to a desired fat content and the container was filled to the desired volume by means of the measuring cylinder. Fifteen milk droplets of the same fat content as the milk in the container were pipetted into the container at a slow regular pace of about 0.5 to 1.0 Hz. This allowed the surface of the diluted milk to settle between each droplet. The acoustic signal from the microphone was then captured using Audacity on the personal computer, and the data were exported as .wav files and imported into Matlab.

By means of Matlab, the audio signals were passed through a series of post processing steps before arriving at $f_m$, i.e. the frequency of the fourth peak D. First the acoustic signal was passed through a peak detector to extract the peaks A, B, C, D. The signal was then windowed to leave just the single splash. Some artefacts were captured here, but were filtered out with a later averaging process. The Fast Fourier Transformation of the splashes were calculated before the average was taken. Outliers were removed at this point and a peak detector was applied across the 0 to 4 kHz range. The fourth peak D, which was found to appear in a range of 1.2 to 3.0 kHz in the experimental setup, was extracted and $f_m$ was set as its frequency location.

The above-described procedure was run for a number of different volume-fat content combinations. Different fat contents were obtained by diluting full fat milk (3.5% fat). The ratio of milk to water was calculated by the following equation, in which $V_w$ represents the volume of water, $V_m$ represents the volume of milk, $C_1$ represents the initial fat content, and $C_2$ represents the final fat content:

$$V_w/V_m = (C_1/C_2) - 1$$

The above equation was derived from the following basic equation:

Concentration=Mass/Volume

When diluting, the mass of fat was kept constant while the volume was changed, hence $$C_1 V_1 = C_2 V_2$$

As already suggested in the foregoing, the invention offers the option of determining milk fat content in real-time during breast milk expression. This allows for separation of expressed milk into foremilk and hindmilk in order to enable more natural feeding, i.e. feeding a baby or infant expressed milk in a similar way to which the milk is extracted by the baby or infant feeding directly at the breast. Several practical considerations are made to actually put this to practice. First, as it is known that expressed human breast milk gradually transitions from less fatty foremilk to more fatty hindmilk, a fat content threshold is used to distinguish between the two types of milk. Due to a lack of an established golden standard for this transition an arbitrary threshold is set at say 4% fat content. Nevertheless, it should be understood that this threshold can readily be changed to a higher or lower value which may be personalized to a lactating woman depending on, for instance, the range of fat content in her expressed milk. Therefore, a 4% fat content threshold is used here solely for purposes of illustration. Second, as it is known that the first milk expressed from a breast is waterier foremilk, the transition point to fattier hindmilk will come after a certain volume of milk has been expressed, prior to the end of the expression session.

Figure 5:
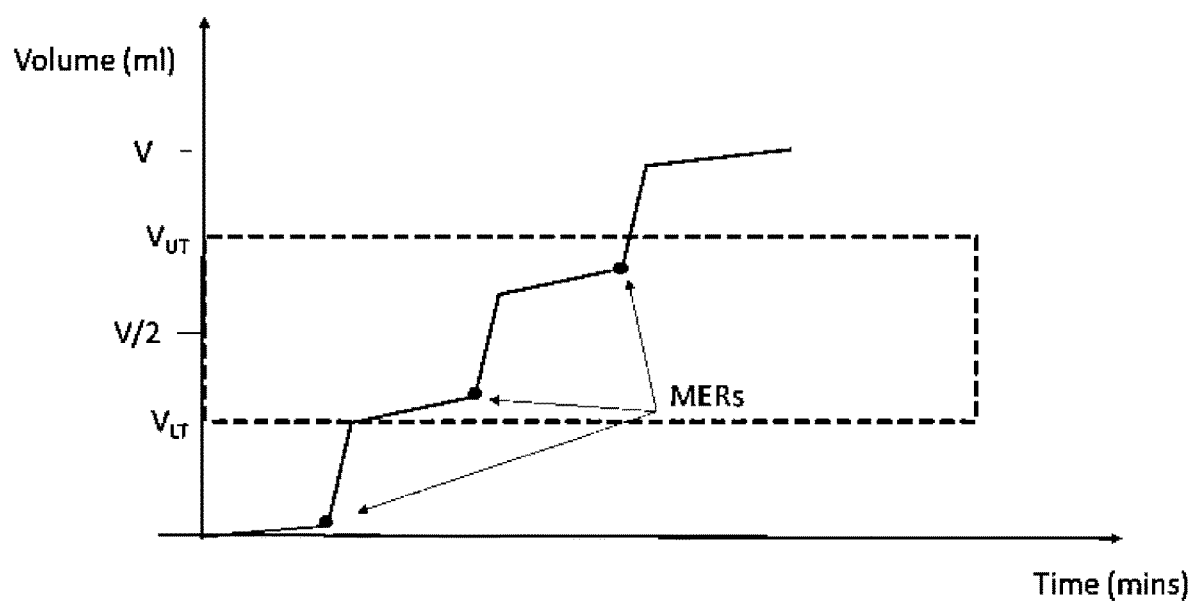
FIG. 5 illustrates how volume thresholds and/or the number of milk ejection reflex events can be used for the purpose of determining a transition between foremilk and hindmilk.

With reference to FIG. 5, it is noted that in order to facilitate the process of finding the transition point, several approaches may be used separately or in combination. In the first place, based on a lactating woman's historical volume of milk expression, volume thresholds may be used to increase the likelihood of finding the transition point. For example, if a lactating woman typically expresses 80 ml per breast, a lower threshold of 25 ml may be used along with an upper threshold of 50 ml. As a result, the transition point between foremilk and hindmilk will be restricted to a narrower 25 ml range. In FIG. 5, $V_{UT}$ represents the upper threshold and $V_{LT}$ represents the lower threshold. In the second place, the number of milk ejection reflex events which have occurred may be used as a basis of finding the transition point. Milk expression is known to be a discontinuous process in which a lactating woman releases milk following successive milk ejection reflex events, which may occur 3 to 5 times during an expression session. By identifying such events based on periods of rapid increases in milk volume followed by periods of very slow increase in milk volume, the transition between foremilk and hindmilk will be easier to determine. For example, the transition is more likely to occur on the second or third milk ejection reflex event than on the first. In FIG. 5, the indication "MERs" is used as to identify the various milk ejection reflex events. A window in which the transition between foremilk and hindmilk takes place is indicated by means of a dashed rectangle.

According to a practical possibility, the lactating woman is notified once the fat content appears to reach 4%, and prompted to switch receptacles so that the fattier hindmilk can be stored separately from the waterier foremilk. This may be done through an app or any other suitable communication means. In practice, the action of switching receptacles may take no more than about 1 minute and may be easily performed by temporarily stopping the pump 31 and then quickly decoupling a first receptacle from the breast pump device 1 and coupling another receptacle to the breast pump device 1 in place of the first one.

During the experiments, the color of the milk was observed changing at different dilutions. In view thereof, a step may be taken for validating the estimated fat content, using optical sensing. For example, a smartphone 7 may be used for acquiring an image of the milk as present in a receptacle 4, which image may then be processed for estimating the fat content of the milk, by correlating with an expected color of the milk.

Data of volume and fat content of the milk could be used to provide coaching or guidance to lactating women. For example, the following may be achieved: i) lactating women may be prevented from ending expression too soon, i.e. before all fat, highly nutritious milk has been extracted, ii) lactating women worrying about the quality of their breast milk may be reassured that the produced volume is sufficient and the quality is alright, as a result of which lactating women may be prevented from quitting breast feeding at an early stage (a too early stage), and iii) expression sessions may be optimized to ensure that the expressed milk is optimized for volume and for fat content, taking into account the assumption that milk expressed relatively quickly or in a relatively short time may have suboptimal volume and fat content than milk expressed at a relatively slower pace.

As suggested earlier, it is known that abnormally large fat globule sizes in breast milk are produced when a lactating woman suffers from mastitis. Assuming that large globule fat size correlates to increased fat content, the fact content tracking technique according to the invention may be used to provide an early warning system for the diagnosis of mastitis. The invention could therefore be applied both for the purpose of mastitis screening as well as monitoring of treatment efficacy.

The acoustic milk expression assessment system 6 could be configured to output relative fat content, i.e. fat content as a percentage of a maximum fat content, rather than absolute fat content. This may be a useful metric to lactating women who want to track the current expression and compare it with previous expressions. This may also allow for simplification of the routine presented above as it would imply that it is not necessary to find the constant $K_2$, which is typically needed for determining the absolute fat content.

As explained above, the milk expression assessment system may be incorporated into a breast pump or it may be part of an external device.

FIGS. 6A to 6E show various possible options. In all case, there is an acoustic sensor 61 for capturing the acoustic signal and a processor 62 for performing an analysis of the acoustic signal by executing a routine thereby to yield an estimation of a value related to the fat content of the milk from the acoustic signal.

Figure 6A:
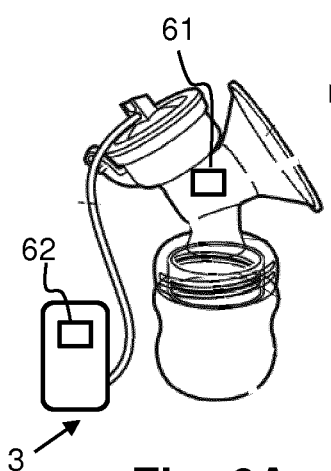
FIGS. 6A to 6E show five possible ways to configure the breast pump device and the acoustic processing.

In FIG. 6A, the milk expression assessment system is integrated into the breast pump device, in the same way as in FIG. 1. The acoustic sensor 61 is located at the expression kit 2 for best acoustic coupling to the sound of the milk droplets. The processor 62 may be anywhere, but is shown as part of the vacuum unit 3 as in FIG. 1. The value related to the fat content of the milk may be displayed by an output interface of the breast pump device or else an external device may be used for more convenient display of information to the user, in the manner shown in FIG. 1. However, the acoustic signal capture and processing takes place as part of the breast pump device.

In one aspect, the invention relates to the breast pump device with the integrated acoustic sensor and processor.

Figure 6B:
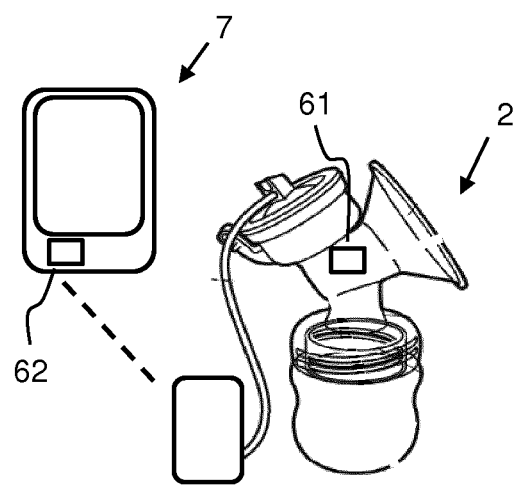

FIG. 6B shows a version where the breast pump device comprises the acoustic sensor 61 but the sensor signal is relayed, preferably wirelessly, to a remote device such as the smartphone 7. The processor of the smartphone 7 then functions as the processor 62 of the system, and the signal processing takes place in the smartphone 7.

In another aspect, the invention relates more generally to the program operated by the processor, and any device in which the suitably programmed processor is incorporated, such as the smartphone 7. Thus, in this aspect, the invention does not include generation of the acoustic signal, but rather relates to the processing of an acoustic signal which is received as an input.

Figure 6C:
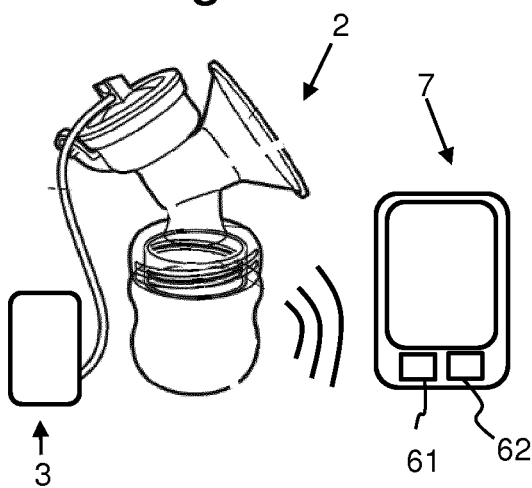

FIG. 6C shows a version where the external device, such as the smartphone 7, incorporates both the acoustic sensor 61 and the processor 62. The microphone of the smartphone is used as the acoustic sensor 61. There may for example be a docking area where the smartphone is placed to receive a consistent audio signal from the expression kit 2, or this may not be necessary if a suitable audio processing algorithm is used. Thus, a completely standard breast pump may be used within this system configuration.

Figure 6D:
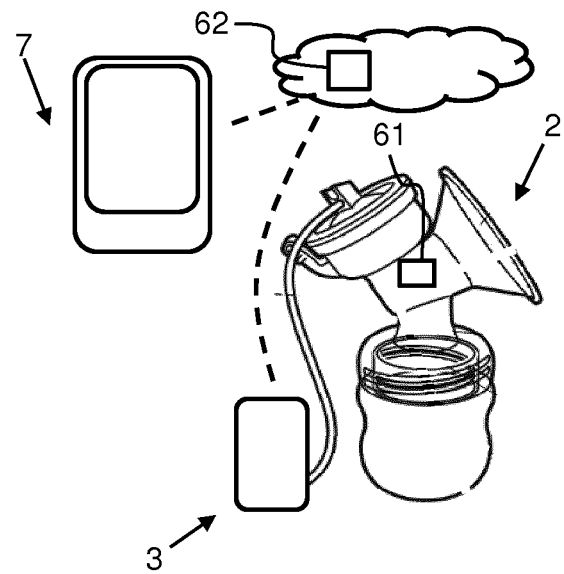

FIG. 6D shows a version where the breast pump device comprises the acoustic sensor 61 but the sensor signal is relayed, preferably wirelessly, to a remote processing center (e.g. a laboratory, as mentioned above), represented as a cloud. The smartphone 7 then retrieves the processing result from the external remote processing center, e.g. over the internet. The remote processing center then performs the function of the processor 62.

Figure 6E:
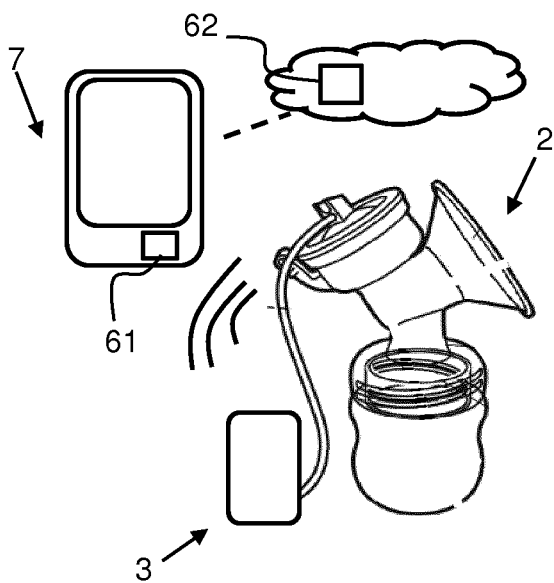

FIG. 6E shows a version where the smartphone comprises the acoustic sensor 61 but the sensor signal is relayed wirelessly, to the remote processing center (e.g. a laboratory, as mentioned above), again represented as a cloud. The smartphone 7 then retrieves the processing result from the external remote processing center, e.g. over the internet. The remote processing center then performs the function of the processor 62. Like FIG. 6C, this enables a standard breast pump to be used.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details which are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

Notable aspects of the invention can be summarized as follows. A breast pump device 1 comprises an expression kit 2 including a breast-receiving funnel 21, a milk outlet 22 and an air outlet 25, and also comprises a vacuum unit 3 configured to realize a pressure cycle in the expression kit 2. For the purpose of obtaining an indication about a fat content of expressed milk, the breast pump device 1 is equipped with an acoustic milk expression assessment system 6, including an acoustic sensor 61 and a processor 62 configured to process an acoustic signal received from the acoustic sensor 61 during operation of the breast pump device 1 when a receptacle 4 is used with the breast pump device 1 for receiving milk from the milk outlet 22 of the expression kit 2. By recording sound during a pumping session, it is possible to determine a frequency shift in the sound of droplets falling down in the receptacle 4 and hitting a surface of the milk contained by the receptacle 4 with respect to a reference situation of a liquid having 0% fat content, which can be taken as a factor in estimating a value related to the fat content of the milk.

The invention claimed is:

1. A method of obtaining an indication about a fat content of milk, wherein at least one liquid droplet is made to fall down on a quantity of the milk, wherein the sound of an event of the liquid droplet hitting a surface of the quantity of the milk is detected so as to obtain an acoustic signal of the event, wherein the method comprises:
performing an analysis of the acoustic signal by executing a routine thereby to yield an estimation of a value related to the fat content of the milk from the acoustic signal;
wherein the analysis of the acoustic signal involves a determination of a frequency spectrum of the acoustic signal.

2. The method according to claim 1, wherein the performing step comprises determining a value of the frequency of at least one peak of the frequency spectrum, and comparing the value to a reference value so as to determine a frequency shift, and using the frequency shift as a factor in estimating a value related to the fat content of the milk.

3. The method according to claim 1, wherein the at least one liquid droplet is a droplet of the milk.

4. A computer program comprising computer program code means which is adapted, when said program is run on a computer, to implement the steps of:
   receiving an acoustic signal of a sound of a liquid droplet hitting a surface of a quantity of milk; and
   performing an analysis of the acoustic signal by executing a routine thereby to yield an estimation of a value related to a fat content of the milk from the acoustic signal, wherein the analysis of the acoustic signal involves a determination of a frequency spectrum of the acoustic signal.

5. A processor which is programmed to run the computer program as claimed in claim 4.

6. A computer program as claimed in claim 4, wherein the performing step comprises determining a value of the frequency of at least one peak of the frequency spectrum, and comparing the value to a reference value so as to determine a frequency shift, and using the frequency shift as a factor in estimating a value related to the fat content of the milk.

7. An apparatus for obtaining an indication about a fat content of milk,
   wherein the apparatus comprises:
   a path for transmittal of an acoustic signal of a sound of a liquid droplet hitting a surface of a quantity of milk, and
   a processor arranged for performing an analysis of the acoustic signal by executing a routine thereby to yield an estimation of a value related to the fat content of the milk from the acoustic signal, wherein the analysis of the acoustic signal involves a determination of a frequency spectrum of the acoustic signal.

8. The apparatus according to claim 7, wherein said at least one liquid droplet is made to fall down on a quantity of the milk within a breast pump device, and wherein:
   the apparatus comprises a device external to the breast pump device; or
   the apparatus comprises an internal part of the breast pump device.

9. The apparatus according to claim 7, further comprising an acoustic sensor for obtaining said acoustic signal.

10. A breast pump device, comprising:
    an expression kit including a breast-receiving funnel and a milk outlet;
    a pump mechanism;
    an acoustic milk expression assessment system including an acoustic sensor for obtaining the acoustic signal, and the apparatus as claimed in claim 7; and
    wherein the processor of the apparatus is configured to perform said analysis of the acoustic signal received from the acoustic sensor during operation of the breast pump device.

11. The breast pump device according to claim 10, wherein the analysis involves determination of a frequency spectrum of the acoustic signal, for example
    determination of a value of the frequency of at least one peak of the frequency spectrum of the acoustic signal and comparison of said value to a reference value so as to determine a frequency shift to be taken as a factor in estimating a value related to the fat content of the milk.

12. The breast pump device according to claim 11, wherein:
    the analysis involves real-time comparison of an estimated value related to the fat content of the milk to a discrimination value, and wherein the processor is configured to issue a warning signal the moment that the estimated value related to the fat content of the milk is found to have increased from below to above the discrimination value; or
    the analysis involves comparison of estimated values related to the fat content of the milk in a period of predetermined length from the start of a pumping session to a threshold value, and wherein the processor is configured to issue a warning signal when the estimated values related to the fat content of the milk are found to be above the threshold value.

13. The breast pump device according to claim 10, wherein the processor is configured to communicate with an external device or system which is separate from the expression kit and the pump mechanism, and which is configured to provide information to a user.

14. The breast pump device according to claim 11, wherein:
    the acoustic sensor is mounted at the expression kit and the processor is mounted at the pump mechanism; or
    the expression kit and the pump mechanism form parts of a breast pump and the breast pump device further comprises a user interface device external to the breast pump, and wherein:
        the acoustic sensor is part of the breast pump and the processor of the acoustic milk expression assessment system is part of the external user interface device; or
        both the acoustic sensor and the processor of the acoustic milk expression assessment system are part of the external user interface device.

15. The apparatus as claimed in claim 7, wherein the processor is arranged for determining a value of the frequency of at least one peak of the frequency spectrum, and comparing the value to a reference value so as to determine a frequency shift, and using the frequency shift as a factor in estimating a value related to the fat content of the milk.

* * * * *